United States Patent
Thennati et al.

(10) Patent No.: US 10,272,131 B2
(45) Date of Patent: Apr. 30, 2019

(54) LINACLOTIDE STABLE COMPOSITION

(71) Applicant: Sun Pharmaceutical Industries Ltd., Mumbai (IN)

(72) Inventors: Rajamannar Thennati, Baroda (IN); Shirish Kulkarni, Baroda (IN); Sanjay Poptani, Baroda (IN); Vimal Kaneria, Baroda (IN); T. Nathamani, Baroda (IN)

(73) Assignee: Sun Pharmaceutical Industries Ltd., Mumbai (IN)

( * ) Notice: Subject to any disclaimer, the term of this patent is extended or adjusted under 35 U.S.C. 154(b) by 34 days.

(21) Appl. No.: 15/503,125

(22) PCT Filed: Aug. 11, 2015

(86) PCT No.: PCT/IN2015/050088
§ 371 (c)(1),
(2) Date: Feb. 10, 2017

(87) PCT Pub. No.: WO2016/024291
PCT Pub. Date: Feb. 18, 2016

(65) Prior Publication Data
US 2017/0232058 A1    Aug. 17, 2017

(30) Foreign Application Priority Data

Aug. 11, 2014    (IN) .......................... 2582/MUM/2014

(51) Int. Cl.
| A61K 38/10 | (2006.01) |
| A61K 9/48 | (2006.01) |
| A61K 47/02 | (2006.01) |
| A61K 47/22 | (2006.01) |

(52) U.S. Cl.
CPC .............. *A61K 38/10* (2013.01); *A61K 9/485* (2013.01); *A61K 9/4858* (2013.01); *A61K 47/02* (2013.01); *A61K 47/22* (2013.01)

(58) Field of Classification Search
None
See application file for complete search history.

(56) References Cited

U.S. PATENT DOCUMENTS

| 8,748,573 B2 | 6/2014 | Fretzen et al. |
| 2010/0048489 A1* | 2/2010 | Fretzen ............... A61K 9/1611 514/1.1 |
| 2013/0045239 A1 | 2/2013 | Johnston et al. |
| 2015/0031632 A1* | 1/2015 | Mo ..................... A61K 9/0056 514/21.1 |

FOREIGN PATENT DOCUMENTS

| WO | WO2010019266 A1 | 2/2010 |
| WO | WO2011019819 A1 | 2/2011 |

OTHER PUBLICATIONS

International Search Report filed for International Publication No. WO2016024291A1 dated Nov. 27, 2015.
Jan Tack et al, "Linaclotide: A new drug for the treatment of chronic constipation and irritable bowel syndrome with constipation" United European Gastroenterology Journal 1(1) 7-20 (2013).

* cited by examiner

*Primary Examiner* — David J Blanchard
*Assistant Examiner* — Daniel F. Coughlin
(74) *Attorney, Agent, or Firm* — Davidson, Davidson & Kappel, LLC

(57) ABSTRACT

A method of stabilizing linaclotide in a solid dosage form, said method comprising
a) preparing a composition of linaclotide, acesulfame and pharmaceutically acceptable excipients and
b) converting the composition into a solid dosage form.

23 Claims, No Drawings

LINACLOTIDE STABLE COMPOSITION

FIELD OF INVENTION

The present invention relates to a method of stabilizing linaclotide in a solid dosage form, said method comprising preparing a composition of linaclotide, acesulfame and pharmaceutically acceptable excipients and converting the composition into a solid dosage form.

BACKGROUND OF THE INVENTION

Linaclotide is useful in irritable bowel syndrome with constipation (IBS-C) and chronic idiopathic constipation (CIC). It is a polypeptide and is susceptible to degradation. Stability of linaclotide dosage forms has presented a significant problem to the formulator. Novel and innovative solution to the problem are required because conventional means of stabilizing a polypeptide have not worked. For example, the label (product information) for presently marketed product, Linzess® capsules, discloses that the product contains a combination of L-leucine and calcium chloride dihydrate which are one of the novel combination of stabilizers claimed in the U.S. Pat. No. 8,748,573. Further the label for Linzess® capsules instructs that the product should be stored at 25° C. (excursions permitted between 15° C. and 30° C.) and further instructs to protect the product from moisture and cautions not to remove desiccant from the container. It is apparent from the literature that linaclotide possesses intrinsic chemical instability (for example, induced by moisture-driven degradation reactions such as hydrolysis, oxidation, deamidation, isomerization, and multimerization) and there lies a need for providing a novel method of preparing a stable solid dosage form of linaclotide with an improved shelf life and robust stability profile.

SUMMARY OF THE PRESENT INVENTION

The present invention provides a method of stabilizing linaclotide in a solid dosage form, said method comprising:
a) preparing a composition comprising linaclotide, acesulfame and pharmaceutically acceptable excipients and
b) converting the composition into a solid dosage form.

Particularly, the present invention relates to a method of stabilizing linaclotide in a solid dosage form, said method comprising,
a) preparing a composition consisting essentially of linaclotide, acesulfame, one or more metal ions or salts thereof and pharmaceutically acceptable excipients and
b) converting the composition into a solid dosage form.

DETAILED DESCRIPTION OF THE INVENTION

The term "stabilizing linaclotide in a solid dosage form" as used herein means that the linaclotide shows less conversion to its degradation products upon storage as compared to a solid dosage form prepared without the use of any stabilizer.

The solid dosage form is also said to be stable when the impurities, such as known and unknown impurities are less than the identification thresholds as recommended by ICH guidelines (International Conferences on Harmonization, Impurities-in new drug products, Q3B(R), by ICH Steering Committee dated 5 Feb. 2003). The known degradation products or known impurities are as follows:

Impurity A: DES-TYR(14)-LINACLOTIDE
H-Cys$^1$Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-OH. cyclic (1→6, 2→10.5→13)-Tris(disulfide)

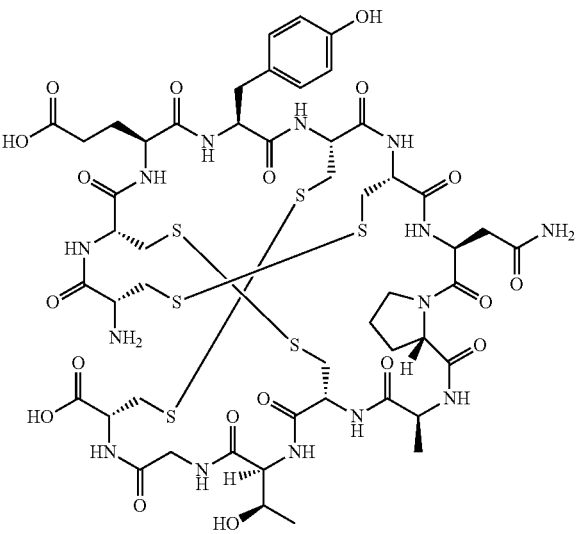 [SMILES: C[C@@H]1NC(=O)[C@@H]2CCCN2C(=O)[C@H](CC(N)=O)NC(=O)[C@@H]2CSSC[C@H](N)C(=O)N[C@H]3CSSC[C@H](NC1=O)C(=O)N[C@@H]([C@@H](C)O)C(=O)NCC(=O)N[C@H](C(=O)O)CSSC[C@H](NC(=O)[C@H](Cc1ccc(O)cc1)NC(=O)[C@H](CCC(=O)O)NC3=O)C(=O)N2]

and Impurity B: ASP (07)-LINACLOTIDE
H-Cys$^1$Cys$^2$-Glu$^3$-Tyr$^4$-Cys$^5$-Cys$^6$-Asp$^7$-Pro$^8$-Ala$^9$-Cys$^{10}$-Thr$^{11}$-Gly$^{12}$-Cys$^{13}$-Tyr $^{14}$-OH. cyclic (1→6, 2→10.5→13)-Tris(disulfide)

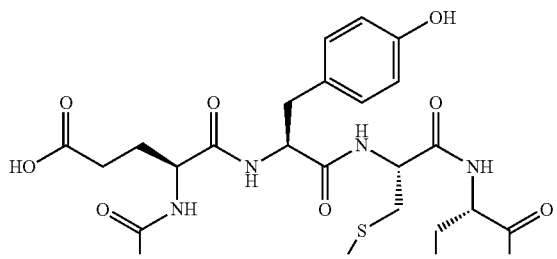

-continued

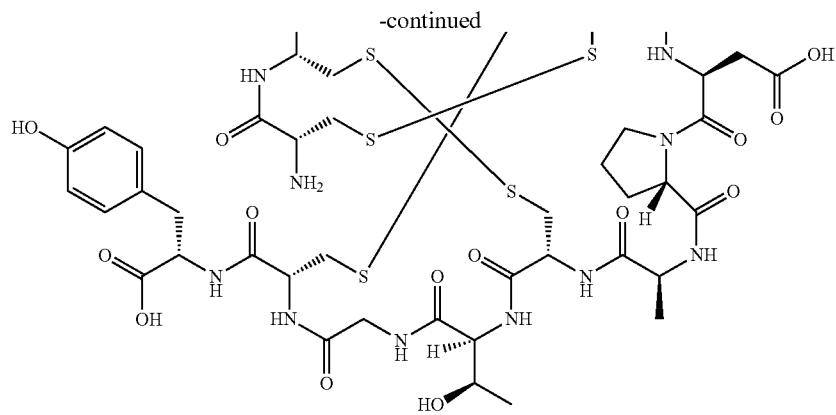

The content uniformity of the solid dosage form may be determined by the standard procedures such as that provided by United States Pharmacopoeia (USP) 34. The solid dosage form is said to be compliant with the USP standards of content uniformity, when the acceptance value of the ten individually tested dosage units are equal or less than the acceptance value L1 of 15. In case, where the dosage form does not comply with this criteria then additional 20 dosage units are individually tested and L2 is determined and dosage form is said to be compliant when the acceptance value is less than or equal to 25.

The moisture or water content of the solid dosage form is determined by standard techniques such as Karl Fischer where loss on drying is determined.

The term 'primary amine' as used herein includes, compounds or excipients having a $NH_2$ group. Such examples, include, but are not limited to, amino acids, such as histidine, cysteine, alanine, amino sugars. The composition according to the present invention consists essentially of linaclotide, acesulfame and one or more metal ions or salts thereof, in that there are no additional stabilizers such as primary amine for example, amino acid, such as histidine, cysteine, alanine, amino sugars and the like and mixtures thereof.

Present inventors have discovered that acesulfame is found to stabilize linaclotide when it is converted into a solid dosage form, in presence of pharmaceutically acceptable excipients. Particularly, the present inventors discovered a method of stabilizing linaclotide in a solid dosage form, said method comprising,
  a) preparing a composition consisting essentially of linaclotide, acesulfame and one or more metal ions or salts thereof and
  b) converting the composition into a solid dosage form.

According to one embodiment of the present invention, the linaclotide is used as its base. The solid dosage form comprises linaclotide in amounts ranging from 0.01 to 1.5 mg, preferably as 0.1 to 0.4 mg per unit dosage form. In specific embodiments the dosage form contains 0.145 mg of linaclotide per unit. In yet another specific embodiment the dosage form contains 0.290 mg of linaclotide in one unit.

The method of stabilizing linaclotide in a solid dosage form according to the present invention includes steps of preparing a composition of linaclotide, acesulfame and pharmaceutically acceptable excipients and converting the composition into a solid dosage form. Acesulfame present in the composition is preferably in form of its pharmaceutically acceptable salts such as acesulfame sodium, acesulfame magnesium, acesulfame calcium or acesulfame potassium salt. Preferably, the acesulfame salt is acesulfame potassium.

In the embodiment, where the potassium salt of acesulfame is used, it is present in amounts ranging from 0.01% to 1.5% by weight of the solid dosage form, preferably 0.5% to 1% by weight of the solid dosage form. The molar ratio of acesulfame or its salt thereof and linaclotide may be in the range from 1:20 to 40:1, preferably 1:2 to 1:9.

Particularly, according to one embodiment of the present invention the method of stabilizing linaclotide in a solid dosage form, comprising,
  a) preparing a composition consisting essentially of linaclotide, acesulfame, one or more metal ions or salts thereof and pharmaceutically acceptable excipients and
  b) converting the composition into a solid dosage form.
The one or more metal ions or its salts are preferably, the metal ions are selected from calcium, magnesium, zinc, aluminum, manganese or mixtures thereof. In one embodiment the solid dosage form includes a divalent metal ion. In one preferred embodiment, the solid dosage form contains calcium chloride dihydrate. The molar ratio of divalent metal ion salt and linaclotide may be in the range from 1:10 to 10:1, preferably 1:3 to 3:1. Alternatively, when a metal ion is present in the composition, it ranges from about 0% to 5%, preferably 0.5% to 3% by weight of the solid dosage form.

According to one specific preferred embodiment, the method of stabilization of linaclotide in a solid dosage form comprises preparing a composition comprising linaclotide, acesulfame, a divalent metal ion and and pharmaceutically acceptable excipients, wherein the solid dosage form shows further improved stability of linaclotide i.e lesser conversion to degradation products upon storage. Also, the solid dosage form is stable in that the impurities, such known and unknown impurities less than the identification thresholds as recommended by ICH guidelines (International Conferences on Harmonization, Impurities-in new drug products, Q3B (R), by ICH Steering Committee dated 5 Feb. 2003).

The solid dosage form prepared according to one specific method comprises preparing composition containing therapeutically effective amount of linaclotide, acesulfame or its salt thereof, a divalent metal ion salt such as a calcium salt and pharmaceutically acceptable excipients.

In a specific embodiment, the method of the present invention provides a solid dosage form, wherein the said method comprising, steps of preparing the composition comprising linaclotide and acesulfame by mixing linaclotide, acesulfame, preferably acesulfame potassium and pharmaceutically acceptable excipients, wherein the composition is free of any compound having primary amine group such as amino acid. Preferably the composition may further include one or more metal ions.

The solid dosage form according to the present invention may further include, one or more antioxidants. Examples of antioxidants that may be used, include but are not limited to, butylated hydroxyl toluene or butylated hydroxyl anisole or mixtures thereof. The antioxidant, when present, ranges from 0.01 to 1% by weight of the solid dosage form.

In the preferred embodiment, the solid dosage form includes pharmaceutically acceptable excipients which are either one or more diluents, wicking agents, granulating agents, binders lubricants, binders or the like and mixtures thereof. Suitable examples of he diluents or fillers include, but are not limited to, polyols, such as mannitol, sorbitol, glycerol, saccharides such as sucrose, trehalose, melizitose, raffinose, and others such as polysorbate, polyethylene glycol ethylene glycol, propylene glycol etc., mannitol, lactose, microcrystalline cellulose, cellulose, propyl cellulose, hydroxypropyl cellulose, hydroxypropyl methyl cellulose, ethyl cellulose, carboxymethyl cellulose and the like. When the solid dosage form is prepared by freeze drying or lyophilization, the water soluble diluents are used as cryoprotectants. Examples of such cryoprotectants, which can be used in the solid dosage form of the present invention include, but are not limited, to polyols, such as mannitol, sorbitol, glycerol, saccharides such as sucrose, trehalose, melizitose, raffinose, and others such as polysorbate, polyethylene glycol ethylene glycol, propylene glycol etc. The suitable diluents which can be used in the present invention include but are not limited to mannitol, lactose, microcrystalline cellulose, cellulose, propyl cellulose, hydroxypropyl cellulose, hydroxypropyl methyl cellulose, ethyl cellulose, carboxymethyl cellulose and the like. In one preferred embodiment, the diluent used is a a sugar alcohol such as mannitol, xylitol, sorbitol or treahalose or combination thereof. In one specific embodiment, mannitol having a particle size such that more than 90% of particles ranging between 75 to 315 µm are used. However, any other suitable diluent may be used. The diluent may range from about 20% to about 99%, preferably, 60% to 90% by weight of the solid dosage form.

Examples of lubricants which may be used in the solid dosage form prepared according to the method of the present invention includes, but are not limited to zinc stearate, calcium stearate, stearic acid and sodium stearyl fumarate, magnesium stearate, talc and waxes and the like and mixtures thereof. The lubricant may range from about 0% to about 10%, preferably, 0.5% to 5% by weight of the solid dosage form.

Suitable wicking agents that may be used in the solid dosage form prepared according to the present invention includes, but are not limited to microcrystalline cellulose, methyl cellulose, sodium carboxymethyl cellulose, methyl cellulose, hydroxypropyl methyl cellulose, ion exchange resins, starch, croscarmellose sodium, crospovidone, calcium silicate, sodium starch glycolate and the like and mixtures thereof. The wicking agent may range from about 0% to about 90%, preferably, 20% to 70% by weight of the solid dosage form. It may be noted that certain diluents that are used have wicking action and are included in both categories.

In one embodiment, the present invention provides a method of stabilizing linaclotide in a solid dosage form, said method comprising,
  a) preparing a composition consisting essentially of linaclotide, acesulfame and one or more metal ions or salts thereof and
  b) converting the composition into a solid dosage form, wherein the composition may be converted into a solid dosage form with the use of a liquid vehicle or without the use of a liquid vehicle.

In certain embodiments, the solid dosage form is converted with the use of liquid vehicle such as for example, water or hydro-alcoholic vehicles. When only water based vehicles are employed, the solid dosage form is converted from the composition by techniques such as lyophilization or freeze drying or spray drying or the like.

According to another embodiment of the present invention, the composition comprising linaclotide and acesulfame is converted into a solid dosage form by a freeze drying process or a spray drying process, wherein the process includes the steps of:
  step i). preparing a solution of linaclotide, acesulfame, optionally, a divalent metal ion salt such as a calcium salt in a suitable liquid vehicle
  step ii). preparing a solid dosage form by spray coating the solution from i). onto inactive excipients or by freeze drying the solution using cryoprotectants.

In one embodiment, the step ii). involves lyophilization or freeze-drying. Typically, the pharmaceutically acceptable excipient is a cryo-protectant such as sugar alcohol like mannitol, and the solvent is aqueous solvent. The aqueous solution of linaclotide, acesulfame, optionally, divalent metal ion salt such as a calcium salt and sugar alcohol like mannitol is filled in a suitable container and subjected to freeze-drying. Preferably the container has a bottom with a large surface area so that the fill height is small and a large surface area is available for efficient drying. Alternatively, in the second step of the process of preparing the solid dosage form, the aqueous solution of linaclotide, acesulfame or its salt thereof, divalent metal ion salt such as a calcium salt and sugar alcohol is poured into molds and freeze-dried by processes as described in U.S. Pat. No. 6,224,905 or as described in WO2009/092703 wherein the process provides a tablet which is rapidly disintegrating.

Particularly, according to one aspect, the process of lyophilisation may be carried out for a period of more than 10 hours such as 20 hours, 40 hours or 50 hours. In one preferred embodiment, the mixture of cryoprotectant, acesulfame potassium, optionally, metal ion or its salt and linaclotide is lyophilized for a period of 45 hours. When such a solid dosage form obtained by the process of lyophilization, is subjected to accelerated stability conditions such as storing for three months at 25° C. and at 60% relative humidity, it was found that linaclotide showed lesser conversion to its degradation products as compared to a solid dosage form prepared without the use of any stabilizer. Also, the solid dosage form is stable as defined herein.

In one aspect of the method of of the present invention, the step ii. of the process involves freeze-drying the solution prepared in step i, blending the freeze-dried mass with additional diluents or fillers, preferably wicking agents or other water adsorbents and then be filled into capsules or compressed into tablets. Suitable diluents or fillers which may be used in the present invention include, but are not limited, to polyols, such as mannitol, sorbitol, glycerol, saccharides such as sucrose, trehalose, melizitose, raffinose, and others such as polysorbate, polyethylene glycol ethylene glycol, propylene glycol,mannitol, lactose, microcrystalline cellulose, cellulose, propyl cellulose, hydroxypropyl cellulose, hydroxypropyl methyl cellulose, ethyl cellulose, carboxymethyl cellulose and the like. Suitable wicking agents that may be used in the present invention include, but are not limited to microcrystalline cellulose, methyl cellulose, sodium carboxymethyl cellulose, methyl cellulose, hydroxypropyl methyl cellulose, ion exchange resins, starch, croscarmellose sodium, crospovidone, calcium silicate, sodium starch glycolate and the like.

The solid dosage form according to the method of the present invention may be prepared by various dry processes that do not use liquid vehicle such as dry mixing and the like. The method of stabilizing linaclotide comprises preparing a composition comprising linaclotide and acesulfame, preferably acesulfame potassium wherein the composition is preferably, prepared by a process which is free of water. Such method includes processes such as for instance, dry mixing. In one specific embodiment, the composition may be prepared by blending linaclotide, acesulfame potassium and optionally, one or more metal ions. Mixing the aforementioned blend with a part of diluent such as sugar alcohol and then further mixing the first blend with the second part of diluent. This blend may be further lubricated with a lubricant. The lubricated dry mix is filled into hard gelatin capsules or filled into a pouch. In another embodiment, the method of the present invention provides a process of preparing the composition wherein the composition is prepared by the process comprising the steps of blending solid linaclotide, acesulfame potassium and optionally, one or more metal ions and converting the mixture into a solid dosage form by dry compaction, compression or granulation into either a powder, pills, pellets, granules, microspheres, microcapsules sachets capsules or tablets. The solid dosage form prepared according to this preferred embodiment, when subjected to accelerated stability conditions for three months at 25° C./60% relative humidity, it was found that linaclotide showed lesser conversion to its degradation products as compared to a solid dosage form prepared without the use of any stabilizer. Also, the solid dosage form is stable as defined herein. This preferred process of preparing the solid dosage form by dry mixing is found to be particularly, advantageous because it is providing a stable composition without the use of an amino acid.

In certain embodiments, the solid dosage form is converted from the composition without the use of any liquid vehicle. Such methods may be dry mixing, dry granulation, roller compaction direct compression of the blend. In such embodiments, the solid dosage form so prepared contains very low amount of water content or may be free of water.

In one specific aspect, the present invention provides a method of stabilizing linaclotide in a solid dosage form, said method comprising preparing the composition by dry mixing process, said process comprising steps of:
a) blending solid linaclotide, acesulfame potassium, optionally, one or more metal ions or its salt and optionally, an antioxidant;
b) mixing the blend of step a), with a diluent;
c) lubricating the mixture of step b) with a lubricant
d) and converting the lubricated mixture of step c) into a solid dosage form such as hard gelatin capsules or compressed tablets,
e) and packaging the solid dosage form into a container having a desiccant therein.

According to this embodiment, the solvent that is used is preferably an aqueous solvent. The solvent may be water or a mixture of water and a water miscible solvent, preferably an alcohol.

According to the method of the present invention, the solid dosage form is prepared by converting the composition comprising linaclotide and acesulfame into a solid dosage form by process of spraying the aqueous solution of linaclotide onto inert solid particles. The inert solid particles may be a pellet, powder, granular material or the like. In one specific embodiment, the solid dosage form is prepared by the process having steps of preparing an aqueous solution containing linaclotide, acesulfame or its salt thereof, divalent metal ion salt such as a calcium salt and a suitable binder such as low viscosity polymer or like. This drug solution is then spray coated on to an inert solid core such as no panel seeds or powder such as lactose. Preferably the second step drying is achieved at a temperature that does not exceed 45° C., and further preferably where an inert gas such as nitrogen or carbon dioxide is used for drying. The dried drug layered core particles are converted into a solid dosage form by either filling into hard gelatin capsules or compressed into tablets or filled into a sachet. In each stage of the process the linaclotide is not exposed to a high temperature. The product temperature preferably does not exceed 45° C. in any step of the process. When such a solid dosage form obtained by the process of spray drying, is subjected to accelerated stability conditions such as storing for three months at 25° C./ 60% relative humidity, the solid dosage form so prepared is found to be stable in that the known and unknown impurities are less than the identification thresholds as recommended by ICH guidelines (International Conferences on Harmonization, Impurities-in new drug products, Q3B(R), by ICH Steering Committee dated 5 Feb. 2003).

The solid dosage form prepared according to the method of the present invention may be in the form of a powder, granules, compacts which may be either filled into hard gelatin capsule or compressed into tablets. In one specific embodiment, the solid dosage form is in the form of powder filled into hard gelatin capsules wherein the moisture content or water content of the filled capsules is less than 1% by weight. In certain embodiments, the method of stabilizing linaclotide in a solid dosage form includes additional packaging of the solid dosage form into moisture resistant means to control the moisture content. Such moisture resistant means include, but are not limited to, bottle/container made up of moisture resistant polymeric materials like high density polyethylene, high density polypropylene and the like. Additionally, the ingress of the moisture may be prevented by use of a desiccant such as activated alumina, calcium sulfate, calcium chloride, bentonite clay, molecular sieves, silica bags, silica pouches or the like.

It is known that obtaining an adequate content uniformity is an important issue especially in pharmaceutical formulations comprising a very low dose of the drug. Because it is difficult to homogenize the active ingredients, especially of very low doses and high bulk density of the pharmaceutically acceptable excipients used in dosage form, difficulties may occur when converting the blend into a solid dosage form such as powder blend filled into the capsules during the process and this may cause inadequate content uniformity of the final dosage forms. The present inventors have surprisingly discovered not only a novel method of stabilizing linaclotide in a solid dosage form but also solved the problem of content uniformity. This is particularly of significance and is an important achievement because linaclotide has microgram level of dose per unit dosage form for eg. merely 145 micrograms or 290 micrograms. The solid dosage form prepared according to the method of the present invention, is not only stable but also has shown adequate content uniformity. The content uniformity of the solid dosage form may be determined by the standard procedures such as that provided by United States Pharmacopoeia (USP) 34. The solid dosage form is said to be compliant with the USP standards of content uniformity, when the acceptance value of the ten individually tested dosage units are equal or less than the acceptance value L1 of 15. In case, where the dosage form does not comply with this criteria then additional 20 dosage units are individually tested and L2 is determined and dosage form is said to be compliant when the acceptance value is less than or equal to 25.

Hereinafter, the invention will be more specifically described with reference to examples. The examples are not intended to limit the scope of the invention and are merely used as illustrations.

EXAMPLES 1 AND 2

TABLE 1 composition details

| | Example 1 | | Example 2 | |
|---|---|---|---|---|
| Ingredients | mg/capsule | % wt./capsule | mg/capsule | % wt./capsule |
| Linaclotide | 0.317 | 0.29 | 0.317 | 0.29 |
| mannitol | 22.100 | 20.09 | 22.100 | 20.09 |
| calcium chloride dihydrate | 1.740 | 1.58 | 1.740 | 1.58 |
| Acesulfame potassium | 0.870 | 0.79 | 0.870 | 0.79 |
| Mannitol | 83.973 | 76.34 | — | — |
| Microcrystalline Cellulose | — | — | 83.973 | 76.34 |
| Magnesium Stearate | 1.000 | 0.91 | 1.000 | 0.91 |

Specified amount of mannitol was added in purified water under stirring to obtain a clear solution. Further calcium chloride dihydrate was added to it and stirring continued for 5 minutes. Acesulfame Potassium was added to the above solution and stirred for 5 minutes. Finally, linaclotide was added to the above solution and stirred for 15 minutes to get a clear solution. This mixture was then freeze dried by keeping suitable parameter settings in lyophilizer for 45 hrs. The lyophilized blend thus obtained was sifted.

The mixture was then blended with Mannitol (Pearlitol SD 200) in case of Example 1 and Microcrystalline Cellulose (Avicel PH 112) in case of Example 2, in a blender for 30 minutes. Magnesium Stearate was sieved and mixed with above blend in a blender for 5 minutes. The blend was then encapsulated in hard gelatin capsules.

The capsules prepared according to Example 1 and Example 2, were subjected to accelerated stability conditions and the chemical analysis was done to determine assay, level of known and unknown impurities.

TABLE 2

Stability data of examples 1 and 2

| EXAMPLE | 25° C./60% Relative humidity | Assay | Water content |
|---|---|---|---|
| 1 | Initial | 98.13 | 1.44 |
| | 3 months | 96.79 | 1.23 |
| 2 | Initial | 97.47 | 5.00 |
| | 3 Months | 98.23 | 4.62 |

It is evident from the data in table 2 that Example 1 and 2 prepared according to the method of the present invention stabilizes linaclotide in the solid dosage form, in that the linaclotide shows less conversion to its degradation products upon storage as compared to a solid dosage form prepared without the use of any stabilizer.

The solid dosage form showed known and unknown impurities less than the identification thresholds as recommended by ICH guidelines (International Conferences on Harmonization, Impurities-in new drug products, Q3B(R), by ICH Steering Committee dated 5 Feb. 2003).

EXAMPLE 3 AND 4

TABLE 3

Details of the composition

| | Example 3 | | Example 4 | |
|---|---|---|---|---|
| Ingredients | mg/capsule | % by weight | mg/capsule | % by weight |
| Linaclotide | 0.290 | 0.26 | 0.290 | 0.26 |
| mannitol | 105.55 | 95.9 | 106.10 | 96.45 |
| calcium chloride dihydrate | 1.74 | 1.58 | 1.74 | 1.58 |
| Acesulfame potassium | 0.87 | 0.79 | 0.87 | 0.79 |
| Butylated Hydroxytoluene | 0.55 | 0.5 | — | — |
| Magnesium Stearate | 1.00 | 0.9 | 1.00 | 0.9 |

Preparation of Example 3: Calcium chloride dihydrate, acesulfame potassium, butylated hydroxytoluene and linaclotide were cosifted together. Mannitol (Pearlitol SD 200) was sieved separately. Then the dry mix blend containing drug and other excipients were geometrically mixed with Mannitol (Pearlitol SD 200), and then sifted. This mixture was blended and lubricated with magnesium stearate and the final blend was encapsulated in hard gelatin capsules. The capsules were further filled into high density polyethylene bottles with three pouches of 1 gm of silica, as a desiccant.

Preparation of Example 4: Calcium Chloride Dihydrate, acesulfame potassium, and linaclotide were cosifted together. Mannitol (Pearlitol SD 200) was sifted separately. Then the dry mix blend containing drug and other excipients were geometrically mixed with Mannitol (Pearlitol SD 200), and then sifted. This mixture was blended and lubricated with magnesium stearate and the final blend was encapsulated in hard gelatin capsules. The capsules were further filled into high density polyethylene bottles with 2 gram of silica, as a desiccant.

The content uniformity was found to be 101.06 (Acceptance Value: 5.59) for example 3 and 98.26 (AV*: 10.99) for example 4 as evaluated by the the modified dimethyl formamide assay method using high performance liquid chromatography. The in vitro dissolution was found to be satisfactory.

TABLE 4

Results of stability of example 3 and 4

| Examples | 25° C./60% Relative humidity | Assay | Water content | Content uniformity** |
|---|---|---|---|---|
| Example 3 | Initial | 103.46 | 0.61 | 101.06 (AV*: 5.6) |
| | 3 months | 100.61 | 0.70 | — |
| Example 4 | Initial | 98.01 | 0.71 | 98.26 (AV*: 11.0) |
| | 3 months | 101.0 | 0.75 | — |

AV* = Acceptance value. As used herein, the term 'content uniformity' or uniformity of content can be used interchangeably.
Content Uniformity** can be determined by the procedure provided in United States Pharmacopoeia (USP) 34. According to USP, the acceptance value of the 10 individually tested units should be equal or less than the acceptance value L1, where L1 is 15. Lesser the value of L1, better is the uniformity of drug content. If the dosage form does not comply with this criteria then additional 20 dosage units are individually tested and L2 is determined and its value should be less than or equal to 25.

The content uniformity was found to be 101.06 and 98.26 with acceptance values of 5.6 and 11, respectively, for examples 3 and 4. The compositions of Example 3 and Example 4, can be inferred to be compliant with the United States Pharmacopoeia (USP) 34 criteria, as the acceptance value is much less than the required value of 15.

It is evident from the data in table 4, that Example 3 and 4 prepared according to the method of the present invention stabilizes linaclotide in the solid dosage form, in that the linaclotide shows less conversion to its degradation products upon storage as compared to a solid dosage form prepared without the use of any stabilizer. The stability testing demonstrated that acesulfame potassium stabilized linaclotide in the solid dosage form.

The solid dosage form showed known and unknown impurities less than the identification thresholds as recommended by ICH guidelines (International Conferences on Harmonization, Impurities-in new drug products, Q3B(R), by ICH Steering Committee dated 5 Feb. 2003).

EXAMPLE 5

| Ingredients | Physical mixture % by weight |
| --- | --- |
| Linaclotide | 25 |
| Acesulfame potassium | 75 |

The specified quantities of linaclotide, acesulfame potassium and inert excipients were mixed together. The physical mixture so prepared was found to be stable.

The invention claimed is:

1. A solid dosage form, comprising a mixture of linaclotide, a stabilizer consisting of acesulfame in an amount in an amount from about 0.5% to about 1% by weight of the solid dosage form to inhibit degradation of the linaclotide and a divalent metal ion or its salt, and at least one pharmaceutically acceptable excipient, the solid dosage form containing the mixture being in the form of a compressed tablet or hard capsule that does not rapidly disintegrate.

2. The solid dosage form of claim 1, further comprising a divalent metal ion salt in a ratio to linaclotide from about 1:3 to about 3:1.

3. The solid dosage form of claim 1, which comprises from about 0.1 to about 0.4 mg linaclotide.

4. The solid dosage form of claim 1, wherein the acesulfame is selected from the group consisting of acesulfame sodium, acesulfame magnesium, acesulfame calcium, acesulfame potassium, and mixtures thereof.

5. The solid dosage form of claim 1, wherein the composition is free of excipients having a $NH_2$ group.

6. A method of stabilizing linaclotide in a solid dosage form, said method comprising:
a) preparing a composition comprising a mixture of linaclotide, a stabilizer consisting of acesulfame or a pharmaceutically acceptable salt thereof in an amount sufficient to inhibit degradation of the linaclotide and a divalent metal ion or its salt, and pharmaceutically acceptable excipients and,
b) converting the composition into a solid dosage form containing the mixture being in the form of a compressed tablet or hard capsule that does not rapidly disintegrate, wherein the acesulfame or a pharmaceutically acceptable salt thereof is in an amount from about 0.5% to about 1% by weight of the solid dosage form.

7. A method as in claim 1, wherein the acesulfame is acesulfame potassium.

8. The method of claim 1, wherein the composition comprises a metal ion or its salts selected from calcium, magnesium, zinc, aluminum, manganese or mixtures thereof.

9. The method of claim 1, wherein the divalent metal ion salt is a calcium chloride dihydrate.

10. The method of claim 1, wherein the composition comprises an antioxidant selected from butylated hydroxyl toluene or butylated hydroxyl anisole or mixtures thereof.

11. The method of claim 1, wherein the solid dosage form is in the form of powder filled into hard gelatin capsules and the water content of the powder is less than 1% by weight.

12. The method of claim 1, wherein the composition is free of excipients having an $NH_2$ group.

13. A linaclotide solid dosage form prepared by the process as claimed in claim 1.

14. A method of stabilizing linaclotide in a solid dosage form, wherein the solid dosage form is prepared by a process comprising the steps of
a) blending a composition of solid linaclotide, a stabilizer consisting of acesulfame or a pharmaceutically acceptable salt thereof and a divalent metal ion or its salt, and pharmaceutically acceptable excipients and
b) converting the composition into a solid dosage form containing the mixture, wherein the acesulfame or a pharmaceutically acceptable salt thereof is in an amount from about 0.5% to about 1% by weight of the composition.

15. A method of stabilizing linaclotide in a solid dosage form as claimed in claim 14, wherein the composition is filled into a packaging that has moisture resistant means.

16. A method of stabilizing linaclotide in a solid dosage form as claimed in claim 14, wherein the solid dosage form is selected from powder, pills, pellets, granules, microspheres, microcapsules, sachets, capsules or tablets, said method not requiring the addition of an aqueous vehicle.

17. A method of stabilizing as in claim 16, wherein the composition is converted into a solid dosage form without the use of a liquid vehicle.

18. The method of claim 14, wherein the composition is free of excipients having a $NH_2$ group.

19. A method of stabilizing linaclotide in a solid dosage form, said method comprising,
a) preparing a composition consisting essentially of a mixture of linaclotide, acesulfame or a pharmaceutically acceptable salt thereof in an amount sufficient to inhibit degradation of the linaclotide, one or more metal ions or salts thereof and pharmaceutically acceptable excipients and
b) converting the composition into a solid dosage form with the use of a liquid vehicle, the solid dosage form containing the mixture being in the form of a compressed tablet or hard capsule that does not rapidly disintegrate, wherein the acesulfame or a pharmaceutically acceptable salt thereof is in an amount from about 0.5% to about 1% by weight of the solid dosage form.

20. A method of stabilizing as in claim 19, wherein the liquid vehicle is free of water.

21. The method of claim 19, wherein the composition is free of excipients having an $NH_2$ group.

22. A method for stabilizing linaclotide in a solid dosage form, the method comprising the step of preparing a composition comprising linaclotide, a stabilizer consisting of acesulfame in an amount sufficient to inhibit degradation of the linaclotide, and a divalent metal ion or its salt, wherein the solid dosage form further comprises at least one pharmaceutically acceptable excipient, the solid dosage form containing the composition being in the form of a compressed tablet or hard capsule that does not rapidly disintegrate, wherein the acesulfame or a pharmaceutically acceptable salt thereof is in an amount from about 0.5% to about 1% by weight of the solid dosage form.

23. The method of claim 22, wherein the composition is free of excipients having an $NH_2$ group.

* * * * *